(12) United States Patent
Currier et al.

(10) Patent No.: US 10,085,840 B2
(45) Date of Patent: Oct. 2, 2018

(54) HYBRID ACETABULAR BEARING FOR ARTIFICIAL HIP

(71) Applicant: Cornerstone Partners LLC, Norwich, VT (US)

(72) Inventors: John H. Currier, Norwich, VT (US); Zachary M. Currier, Norwich, VT (US)

(73) Assignee: Cornerstone Partners LLC, Norwich, VT (US)

( * ) Notice: Subject to any disclaimer, the term of this patent is extended or adjusted under 35 U.S.C. 154(b) by 0 days.

(21) Appl. No.: 14/377,698

(22) PCT Filed: Feb. 11, 2013

(86) PCT No.: PCT/US2013/025589
§ 371 (c)(1),
(2) Date: Aug. 8, 2014

(87) PCT Pub. No.: WO2013/120080
PCT Pub. Date: Aug. 15, 2013

(65) Prior Publication Data
US 2015/0351918 A1    Dec. 10, 2015

Related U.S. Application Data

(60) Provisional application No. 61/597,546, filed on Feb. 10, 2012.

(51) Int. Cl.
*A61F 2/34* (2006.01)
*A61F 2/46* (2006.01)
(Continued)

(52) U.S. Cl.
CPC .............. *A61F 2/34* (2013.01); *A61F 2/4637* (2013.01); *A61F 2002/30014* (2013.01);
(Continued)

(58) Field of Classification Search
CPC .... A61F 2/32; A61F 2/34; A61F 2002/30515; A61F 2002/30495; A61F 2002/30497; A61F 2002/30663; A61F 2002/3208
See application file for complete search history.

(56) References Cited

U.S. PATENT DOCUMENTS 4,770,658 A * 9/1988 Geremakis ................ A61F 2/32
623/22.19
4,784,663 A    11/1988 Kenna
(Continued)

FOREIGN PATENT DOCUMENTS

WO    WO-03/092557 A2    11/2003
WO    WO-2007/079521 A1    7/2007

OTHER PUBLICATIONS

International Search Report and Written Opinion for International Patent Applicaiton No. PCT/US2013/25589, dated Jun. 12, 2013 (15 pages).

(Continued)

*Primary Examiner* — Marcia Watkins
(74) *Attorney, Agent, or Firm* — Clark & Elbing LLP

(57) ABSTRACT

The invention features acetabular components for an artificial hip. The invention also features methods and tools for assembling a hip prosthesis that includes the acetabular components of the invention.

14 Claims, 14 Drawing Sheets

(51) Int. Cl.
*A61F 2/30* (2006.01)
*A61F 2/32* (2006.01)

(52) U.S. Cl.
CPC ............ *A61F 2002/30016* (2013.01); *A61F 2002/30332* (2013.01); *A61F 2002/30337* (2013.01); *A61F 2002/30495* (2013.01); *A61F 2002/30515* (2013.01); *A61F 2002/30695* (2013.01); *A61F 2002/30934* (2013.01); *A61F 2002/325* (2013.01); *A61F 2002/3241* (2013.01); *A61F 2002/4627* (2013.01); *A61F 2002/4628* (2013.01)

(56) References Cited

U.S. PATENT DOCUMENTS

| | | | |
|---|---|---|---|
| 4,795,471 A * | 1/1989 | Oh | A61F 2/32 623/22.19 |
| 5,062,853 A | 11/1991 | Forte | |
| 5,092,897 A | 3/1992 | Forte | |
| 5,263,988 A | 11/1993 | Huebner | |
| 5,314,491 A * | 5/1994 | Thongpreda | A61F 2/32 623/22.29 |
| 6,682,567 B1 | 1/2004 | Schroeder | |
| 8,114,166 B2 * | 2/2012 | Auxepaules | A61F 2/4684 623/22.28 |
| 2005/0171614 A1 * | 8/2005 | Bacon | A61F 2/30771 623/22.19 |
| 2006/0167556 A1 | 7/2006 | Lazennec et al. | |

OTHER PUBLICATIONS

Extended European Search Report for European Patent Application No. 13746376.6, dated Sep. 15, 2015 (7 pages).

* cited by examiner

HYBRID ACETABULAR BEARING FOR ARTIFICIAL HIP

BACKGROUND

Approximately 300,000 artificial hips are implanted annually, in the United States alone. An increasing number of younger, more physically active patients has prompted the orthopedic implant industry to develop more durable, wear-resistant bearing materials, for example, metal-on-metal or ceramic-on-ceramic bearings. However, although demand for low volumetric wear of hard-on-hard bearings remains strong, sales of metal-on-metal bearings has declined, due to concerns about severe adverse tissue reaction to metal ions and metal debris. For example, the August 2010 recall of the ASR™ hip by DePuy has focused intense media, technical publication and legal scrutiny on metal-on-metal bearings across the industry.

Ceramic-on-ceramic bearings are an alternative solution; however, those bearings have also suffered a major setback over the last 4 years, due to a growing incidence of in vivo squeaking.

SUMMARY

Metal on metal ("MOM") hips are currently under scrutiny due to reportedly high failure rates. Recent analysis of retrieved, MOM hip bearings shows wear and damage features that suggest edge loading of artificial hips under a variety of in vivo conditions, and which may be associated with pain and instability. See J. Currier et al., *Gouge features on Metal-on-Metal hip bearings can result from high stresses during rim contact*, included in the attached Appendix, which forms a part of this disclosure.

Ceramic on ceramic ("COC") hips are also susceptible to edge loading. The metal rim of a conventional acetabular cup can scrape off onto a ceramic femoral head when the femoral head is reduced into the acetabular cup (and ceramic liner) during surgery. Metal on the ceramic head may be a factor in painful, unstable and/or squeaking ceramic-on-ceramic ("COC") hips. See J. Currier et al., *A proposed mechanism for squeaking of ceramic-on-ceramic hips*, Wear (2010), doi: 10.1016/j.wear.2010.08.006, Elsevier B. V. See also I. Tomek, et al., *Metal Transfer on a Ceramic Head With a Single Rim Contact, The Journal of Arthroplasty* Vol. 27 No. 2 2012, Elsevier, Inc., both included in the attached Appendix.

Conventional artificial hips feature an intentional mismatch between the internal acetabular cup diameter and the diameter of the femoral head, in order to allow for lubrication by synovial fluid. However, this mis-match allows a roll/slide mechanism when the hip is flexed—flexion occurs by rolling and sliding of the head within the cup/liner. The roll/slide of the head in the cup has been demonstrated in vitro to cause the hip to vibrate at an audible frequency, and may also be a causative factor in squeaking hips.

The hybrid bearing surface acetabular component described herein addresses the problem of edge loading by providing a modular acetabular bearing for an artificial hip. The modular bearing includes a hybrid articular surface with a central (polar) portion made of a relatively high hardness material (e.g., metal or ceramic), and an outer, circumferential portion made of a more compliant, tougher material, such as ultrahigh molecular weight polyethylene. The hybrid bearing surface combines high wear resistance of the hard material in the region of the bearing where relatively high-velocity articulation occurs during gait, with compliance and toughness at and near the rim of the acetabular cup where bearing contact occurs during gait reversal and reseating of the femoral head following micro-separation. The outer, circumferential portion may also be self-lubricating, for example where polyethylene is used, and may extend over the hard cup rim, to prevent contact and scraping between the hard rim and the femoral head (e.g., during reduction during surgery or reduction following any dislocation or micro-separation). The hybrid bearing surface acetabular component thus minimizes or eliminates the detrimental tribological effects of edge loading of hard-on-hard hip arthroplasty bearings.

The disclosed hybrid bearing may also fit more tightly against the femoral head than do conventional bearings, such that rolling of the femoral head within the cup portion of the bearing is limited or prevented, thus reducing audible squeak.

In one embodiment, a hybrid bearing surface acetabular component includes an acetabular cup for fitting with a patient's acetabulum. A hybrid bearing fits with the acetabular cup. The hybrid bearing has a polar portion for fitting with a lower section of the acetabular cup, and a rim bearing for fitting with an upper section of the acetabular cup and atop the polar portion. A locking component displaces the rim bearing radially outward against an interior surface of the upper section, to secure the hybrid bearing within the acetabular cup.

In one embodiment, a hybrid bearing surface acetabular component, includes an acetabular cup for fitting with a patient's acetabulum. The acetabular cup has a lower section defined by a morse taper profile about an inner circumference thereof, and a upper section having a circumferential reverse tapered portion therein. A hybrid bearing fits with the acetabular cup, and includes a polar portion for fitting within the lower section and a rim bearing for fitting with the upper section. The polar portion has an edge about its outer circumference that is complementary to the morse taper profile, and the rim bearing has a circumferential groove and an angled sidewall for fitting against the reverse tapered portion of the acetabular cup. A rim of the rim bearing covers a rim of the acetabular cup, when the rim bearing is inserted in the upper section. A locking component fits between two open ends of the rim bearing, to secure the rim bearing against the reverse tapered portion and within the upper section.

DETAILED DESCRIPTION

Figure 1:
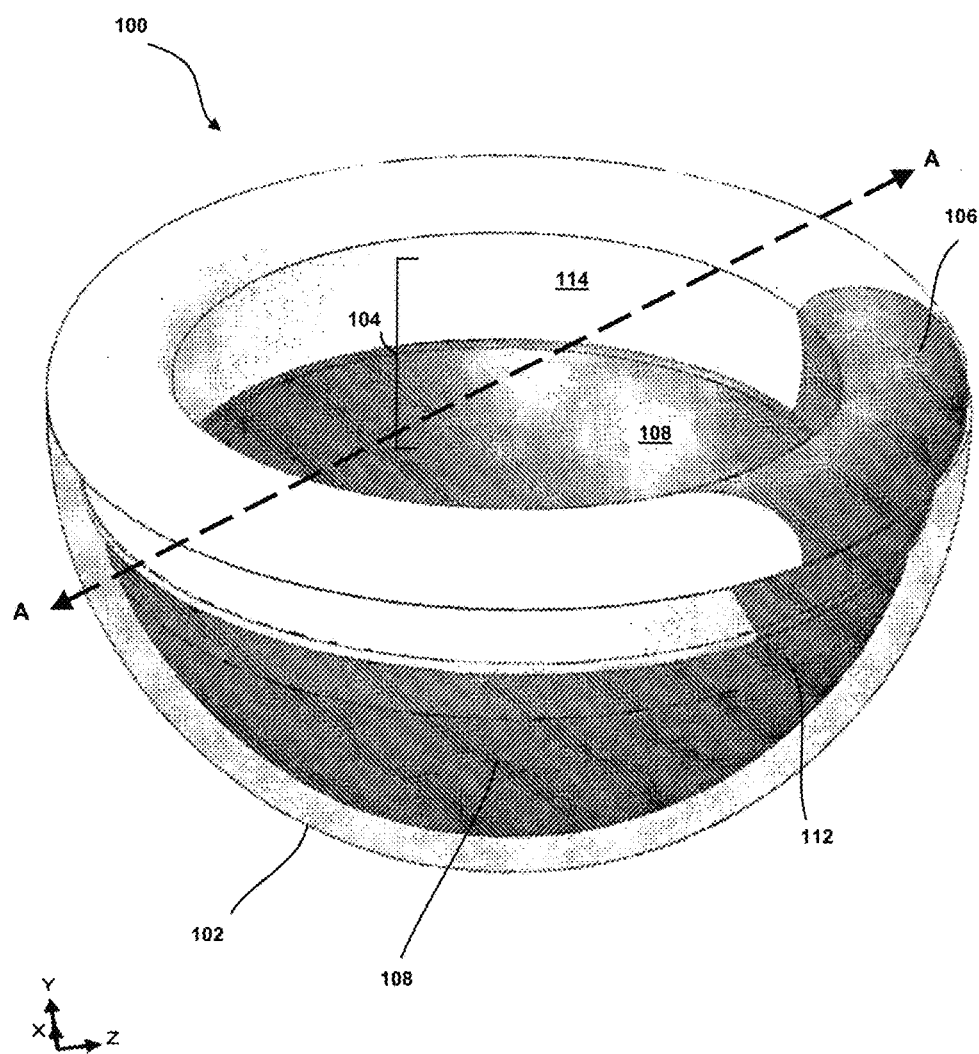
FIG. 1 is a perspective view of a hybrid bearing surface acetabular component including an acetabular cup, hybrid bearing and locking component, according to an embodiment.

FIG. 1 shows a hybrid bearing surface acetabular component 100, including an exterior acetabular cup 102, a hybrid bearing 104 and a locking component or keystone 106 ("locking component" and "keystone" may be used interchangeably hereafter with reference number 106). FIGS. 2-7 show additional detail of cup 102, hybrid bearing 104 and keystone 106; thus, FIGS. 1-7 are best viewed together with the following description. Hybrid bearing 104 includes a polar bearing portion 108 that is inserted into cup 102 such that an upper, circumferential edge 110 of polar portion 108 aligns with an inner, circumferential Morse taper type profile 112. Morse taper profile 112 tapers slightly inward toward the pole of cup 102. A rim bearing portion 114 fits into cup 102 atop a rim 111 of polar portion 108, in particular, against an upper, internal reverse-tapered portion 116 about the upper circumference of cup 102. Keystone 106 biases rim bearing 114 outward against the interior of cup 102 to secure hybrid bearing 104 with cup 102. In one aspect, rim bearing portion 114 and polar portion 108 are made of different materials. Polar portion 108 is for example made of a hard material, such as metal or ceramic, while rim bearing 114 may be ultrahigh molecular weight polyethylene or another material that is relatively more compliant than the material of polar portion 108. Rim bearing 114 accommodates edge loading of the femoral head and/or impingement of the femoral neck on an edge of component 100. Ultrahigh molecular weight polyethylene is self-lubricating and relatively compliant, and will therefore not bind the head by virtue of diametral contact in the same way a conventional hard bearing would do.

Figure 2:
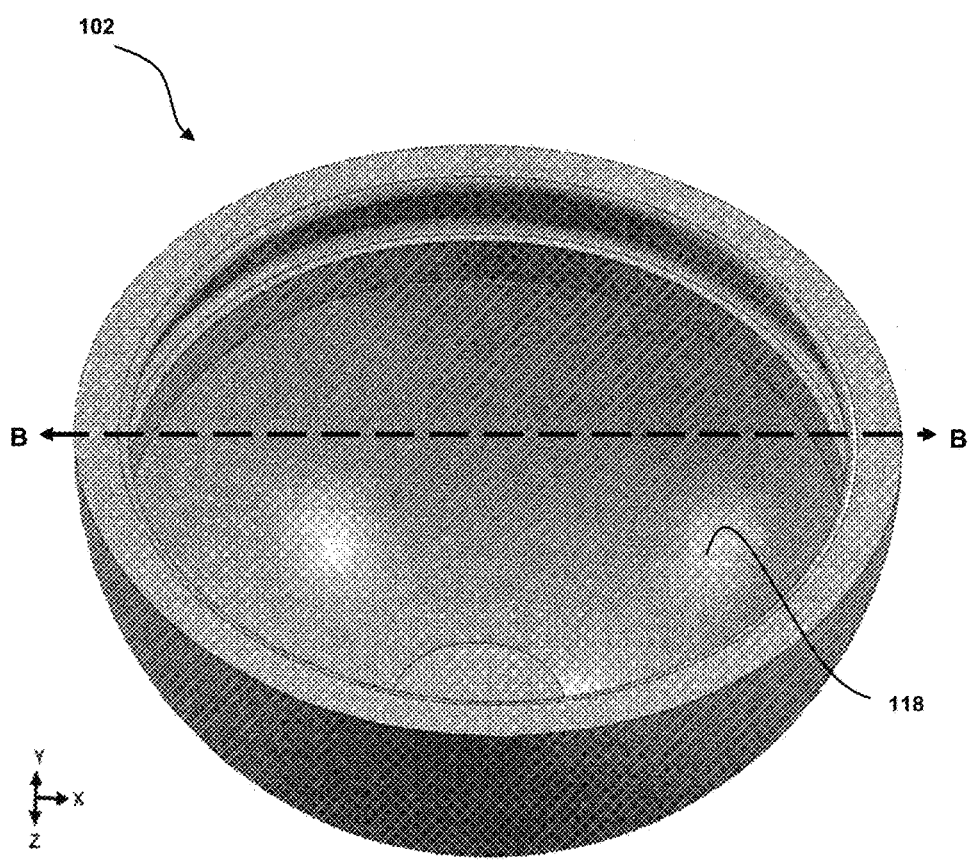
FIG. 2 is a perspective view of the acetabular cup of the hybrid bearing surface acetabular component of FIG. 1.
Figure 3:
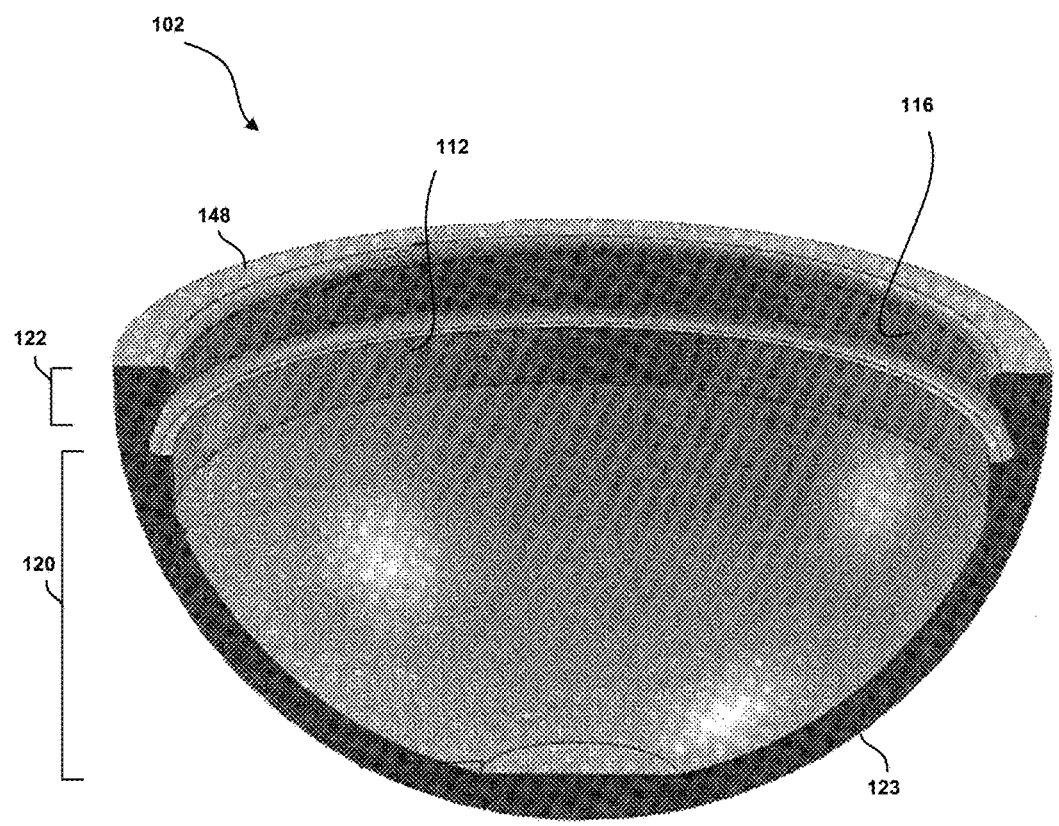
FIG. 3 is a cross-sectional view of the acetabular cup of FIGS. 1 and 2, illustrating a reverse tapered profile and taken along line B--B of FIG. 2.

As shown in FIGS. 2-3, acetabular cup 102 has a hollow interior 118 for accepting hybrid bearing 104. A lower section 120 accepts polar portion 108 of hybrid bearing 104. An upper section 122 above lower section 120 has a diameter greater than the largest diameter of lower section 120. Rim bearing 114 fits against reverse tapered portion 116 of upper section 122. When fitted into lower section 120, polar portion 108 may form a shelf to enhance support of rim bearing 114 in upper section 122. Acetabular cup 102 is affixed to a patients acetabulum, for example using bone cement or an ingrowth surface such as a porous coating. In one aspect, an exterior surface 123 of cup 102 is roughened or textured to increase surface area available for bonding. In another aspect, exterior surface 123 may be treated with hydroxyapatite or other materials that promote osseointegration. Acetabular cup is preferably made of biocompatible metal, such as titanium; however, other sufficiently strong, biocompatible materials may be utilized in addition to or as an alternative to metal.

Figure 4:
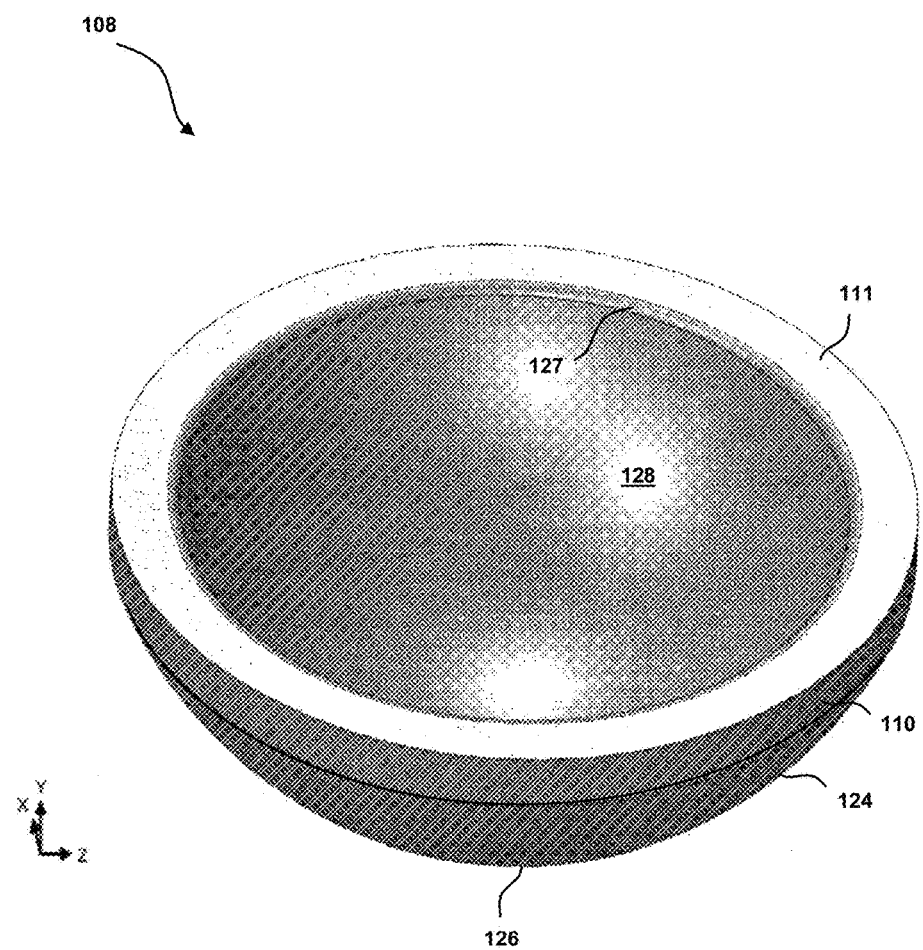
FIG. 4 is a perspective view of a polar portion of the hybrid bearing shown in FIG. 1, according to an embodiment.

FIG. 4 is a perspective view showing polar portion 108 of hybrid bearing 104. In one aspect, edge 110 extends upward (i.e., vertically or near vertically) from the exterior of a lower body 124 of portion 108 (when body 124 stands on an end 126) and terminates in rim 111, such that, when inserted into cup 102, edge 110 fits with Morse taper profile 112 and rim 111 provides support for rim bearing 114. However, it will be appreciated that angles and shape of both polar portion 108 and profile 112 may be altered, so long as portion 108 and profile 112 are complementary. Polar portion 108 may include a chamfered inner edge 127 between rim 111 and the interior of lower body 124. Chamfered inner edge 127 for example reduces stress concentration at the interface between polar portion 108 and rim bearing 114 and provides a recession into which any debris can be swept from an articular surface 128 of polar portion 108/assembled component 100.

Figure 5:
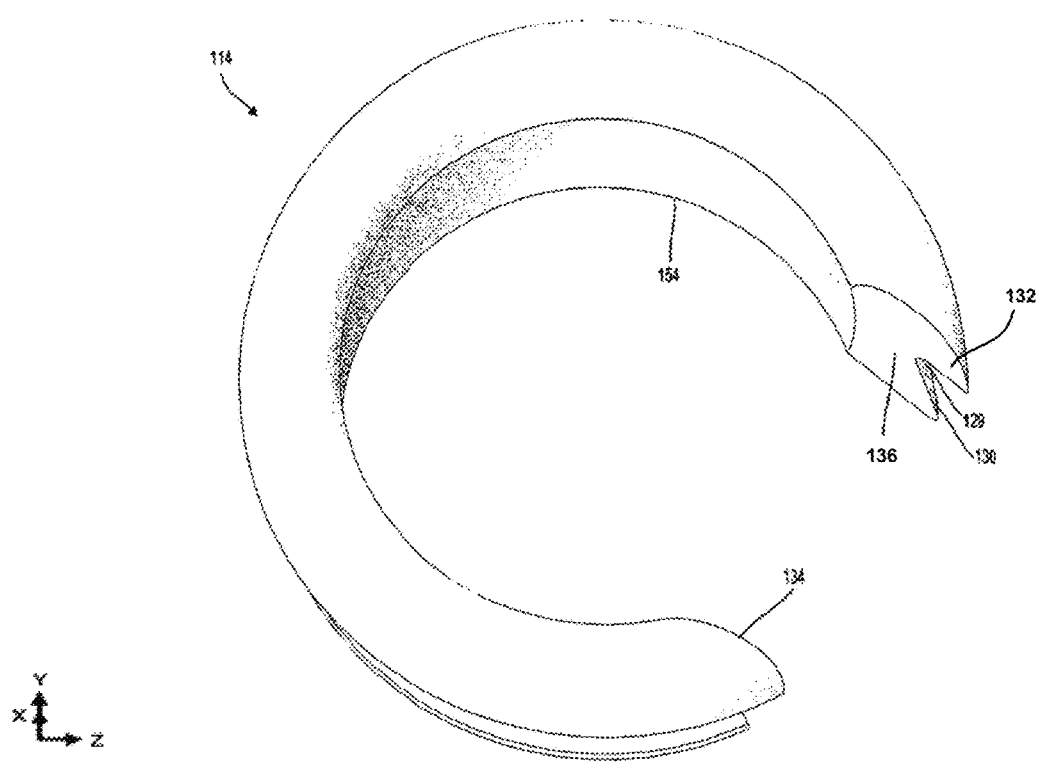
FIG. 5 is a perspective view of a rim bearing of the hybrid bearing of FIG. 1, according to an embodiment.
Figure 6:
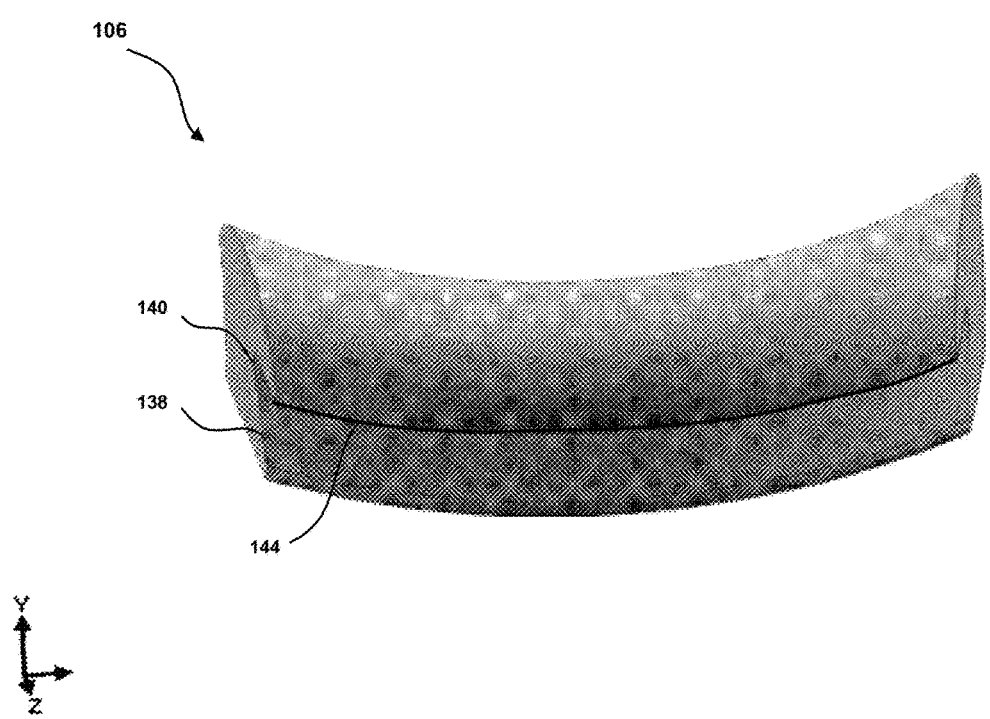
FIG. 6 is a perspective view of the locking component of FIG. 1, according to an embodiment.

FIG. 5 is a perspective view of rim bearing 114. Rim bearing 114 forms an arc having a circumferential groove 129 and angled, outer sidewall 130 extending downward beneath a lip 132. While rim bearing 114 is shown as a single segment, it will be appreciated that rim bearing 114 may alternately include multiple segments that abut or fit together to line upper section 122 of acetabular cup 120. When inserted in upper section 122 of acetabular cup 102 (i.e., above polar portion 108 in lower section 120), groove 129 and angled sidewall 130 fit with reverse tapered portion 116 (see, e.g., FIG. 10). As shown, rim bearing 114 is open-ended. This allows compression of rim bearing 114, for example by pressing open ends 134, 136 towards one another, to facilitate insertion of rim bearing 114 into acetabular cup 102.

Locking component or keystone 106 (FIG. 6) fits between open ends 134, 136 and has the same or similar outer profile as rim bearing 114. For example, angled sidewall 138 and a groove 140 of keystone 106 are identical in shape, position, depth and angle (as appropriate) to sidewall 130 and groove 129 of rim bearing 114. Thus, rim bearing 114 and keystone 106 need not be aligned with any particular features of upper section 122 to fit with reverse tapered portion 116.

In another aspect, angled sidewall 138 may include one or more protrusions (not shown) sized to mate with indentations or holes in reverse tapered portion 116 of cup 102, to provide rotational adjustability of rim bearing 114. For example, a series of indentations or holes (also not shown) may be placed about reverse tapered portion 116 of cup 102 such that keystone element 106, and thus rim bearing 114, may be selectively placed and fixed. It will be appreciated that other aspects of keystone 106's geometry may be different than what is shown in the drawings.

In practice, rim bearing 114 may be inserted into cup 102 intra-operatively. As rim bearing 114 and keystone 106 form two or more circumferential segments, rim bearing 114 may be compressed, inserted into cup 102 and then displaced radially outward into reverse tapered portion 116. Keystone 106 may be inserted between open ends 134, 136 to complete the circumference of hybrid bearing 104 and maintain position of rim bearing 114 within cup 102. Keystone 106 locks rim bearing 114 outward and prevents radially inward displacement of rim bearing 114. In one aspect, keystone 106 is placed with cup 102 following insertion of rim bearing 114. Keystone 106 may be affixed to acetabular cup 102, to prevent rotational motion of rim bearing 114 relative to acetabular cup 102. This for example allows intra-operative placement and adjustment of a rim bearing that is not axially symmetric, but has varying geometries, such as raised or lowered areas on the rim. Axially asymmetric rim bearings might for example be used by a surgeon to tailor bearing alignment to the anatomy of an individual patient or to the existing alignment of other components in the hip device.

In another aspect, keystone 106 may first be placed with cup 102, and alternately, permanently or temporarily affixed with cup 102, and rim bearing 114 then compressed, inserted into the cup and displaced outwards to abut and/or join with keystone 106 and cup 102. Reverse tapered portion 116 prevents dissociation of rim bearing 114 out of cup 102 by edge loading or distraction forces imposed by the femoral head.

In another aspect, keystone 106 and/or rim bearing 114 may include features that fit with features of upper section 122, such that a specific orientation between upper section 122 and keystone 106/rim bearing 114 must be achieved in order to secure rim bearing 114 and keystone 106 with acetabular cup 102.

Figure 7:
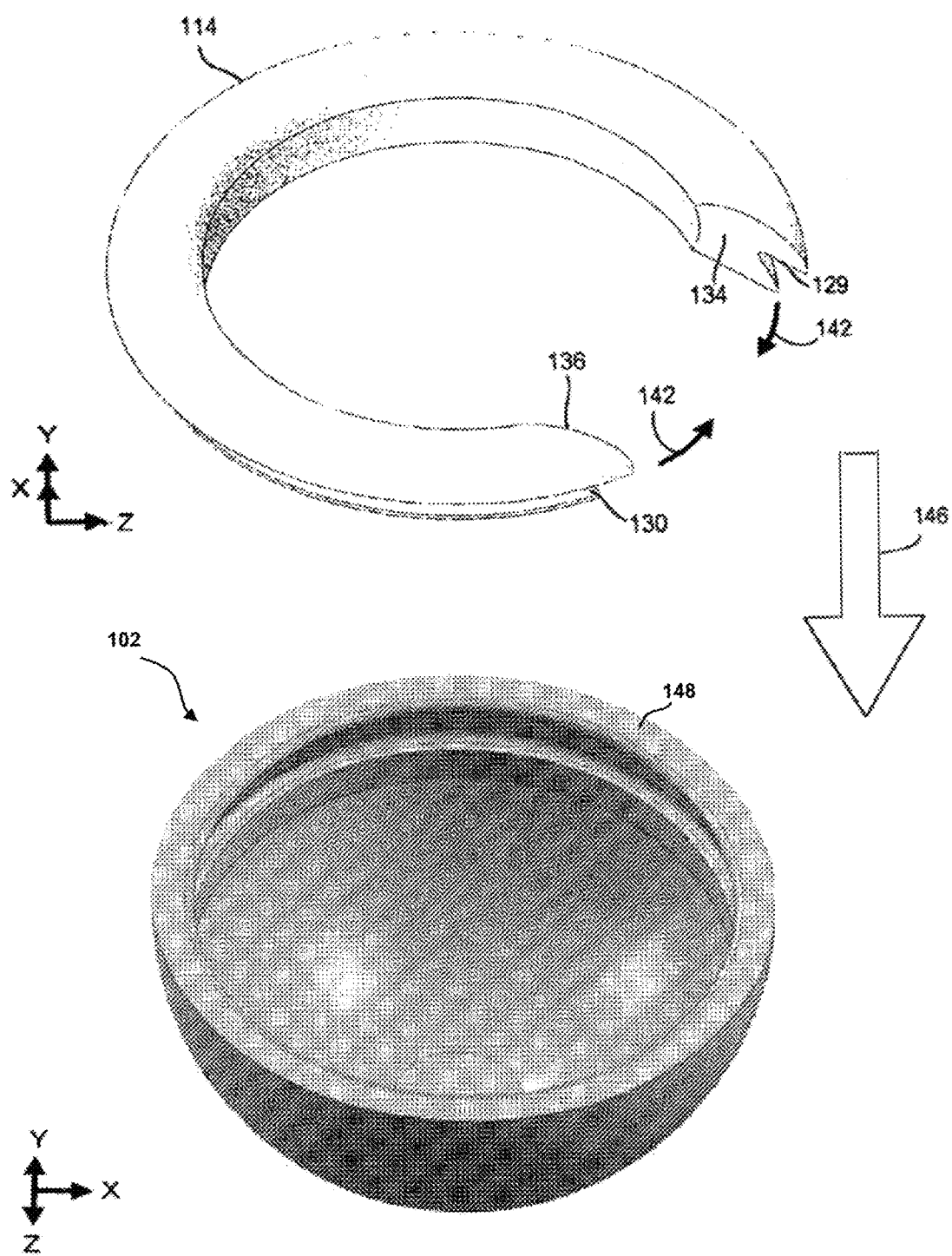
FIG. 7 is a perspective view illustrating inward compression of the rim bearing of FIG. 5 prior to insertion into the acetabular cup of FIGS. 1 and 2, according to an embodiment.

In practice, rim bearing 114 may be pinched or compressed to move open ends 134, 136 together, as indicated by arrows 142, FIG. 7, reducing the effective circumference of rim bearing 114 so that it can be inserted into upper section 122 (arrow 146), with groove 129 and angled sidewall 130 fitting with reverse tapered portion 116. Ends 134, 136 are released and allowed to spring or otherwise move out into alignment with the portion 116. Keystone 106 is inserted between ends 134, 136 and with its groove 140 and sidewall 138 conforming to reverse tapered portion 116. Keystone 106 biases or holds rim bearing 114 against reverse tapered portion 116, to lock bearing 114 in place. In addition, rim bearing 114 may itself be biased towards an "open" position such that it springs back to its original shape when ends 134, 136 are released. When in place, lip 132 of rim bearing 114 extends over a rim 148 of acetabular cup 102, covering cup rim 148 to prevent contact of a femoral head with hard cup rim 148. Likewise, a lip 144 of keystone segment 106 covers cup rim 148 when inserted into acetabular cup 102. Preventing contact between the femoral head and hard rim 148 may reduce or eliminate wear stripes caused by edge loading of conventional ceramic-on-ceramic hips, and may further interrupt the roll/slide vibration mechanism that contributes to in vivo squeaking.

Rim bearing 114 and keystone segment 106 may be sized to extend to greater than hemispherical coverage of the femoral head, thereby constraining the head against distraction or micro-separation during gait and further mitigating detrimental effects of edge loading. Forming rim bearing 114 of a relatively compliant material may allow an interference fit of the femoral head into a sub-hemispherical outer opening of the rim bearing during reduction of the hip in surgery.

Figure 8:
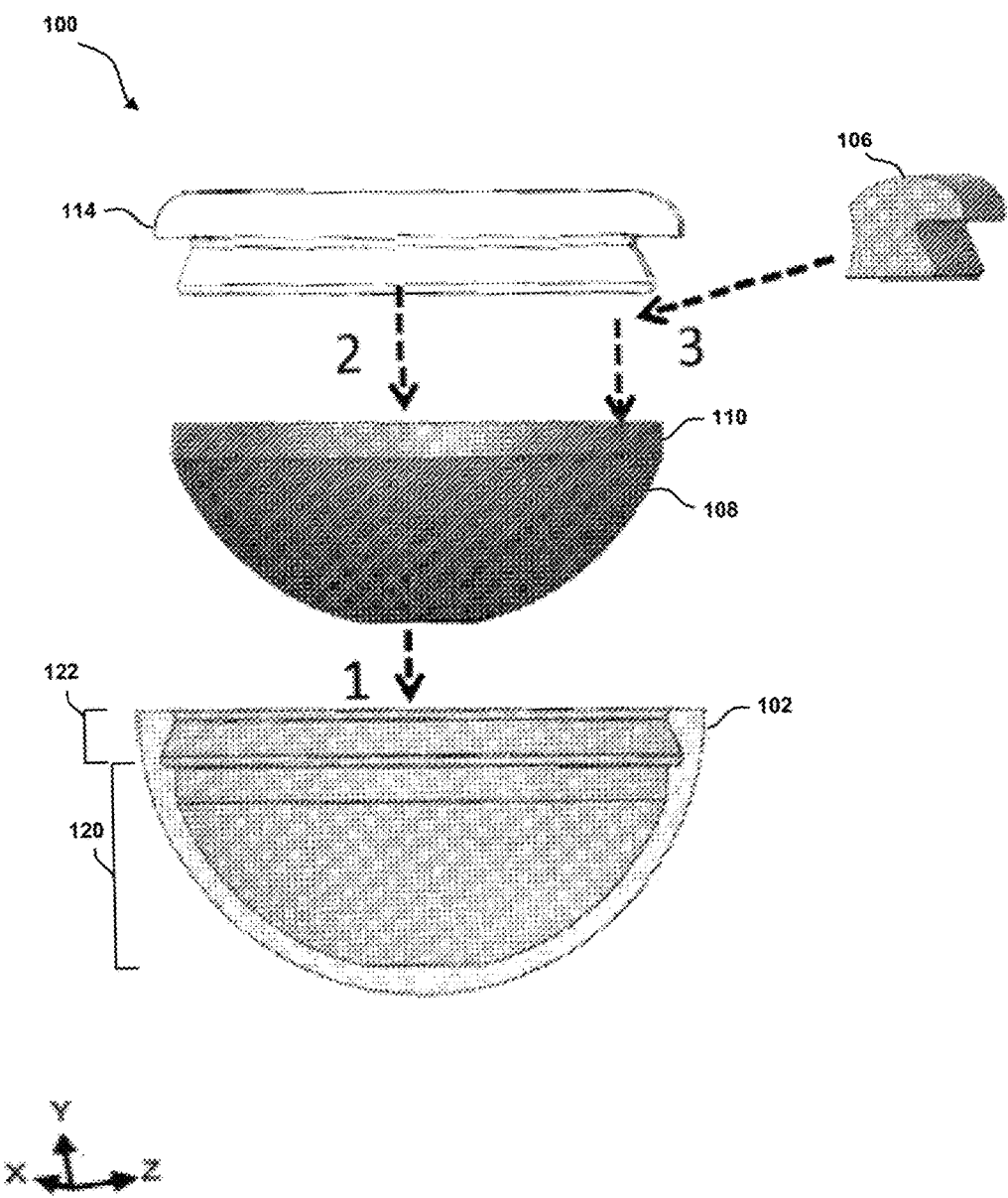
FIG. 8 is a pre-assembly side view of the hybrid bearing surface acetabular component of FIG. 1.
Figure 9:
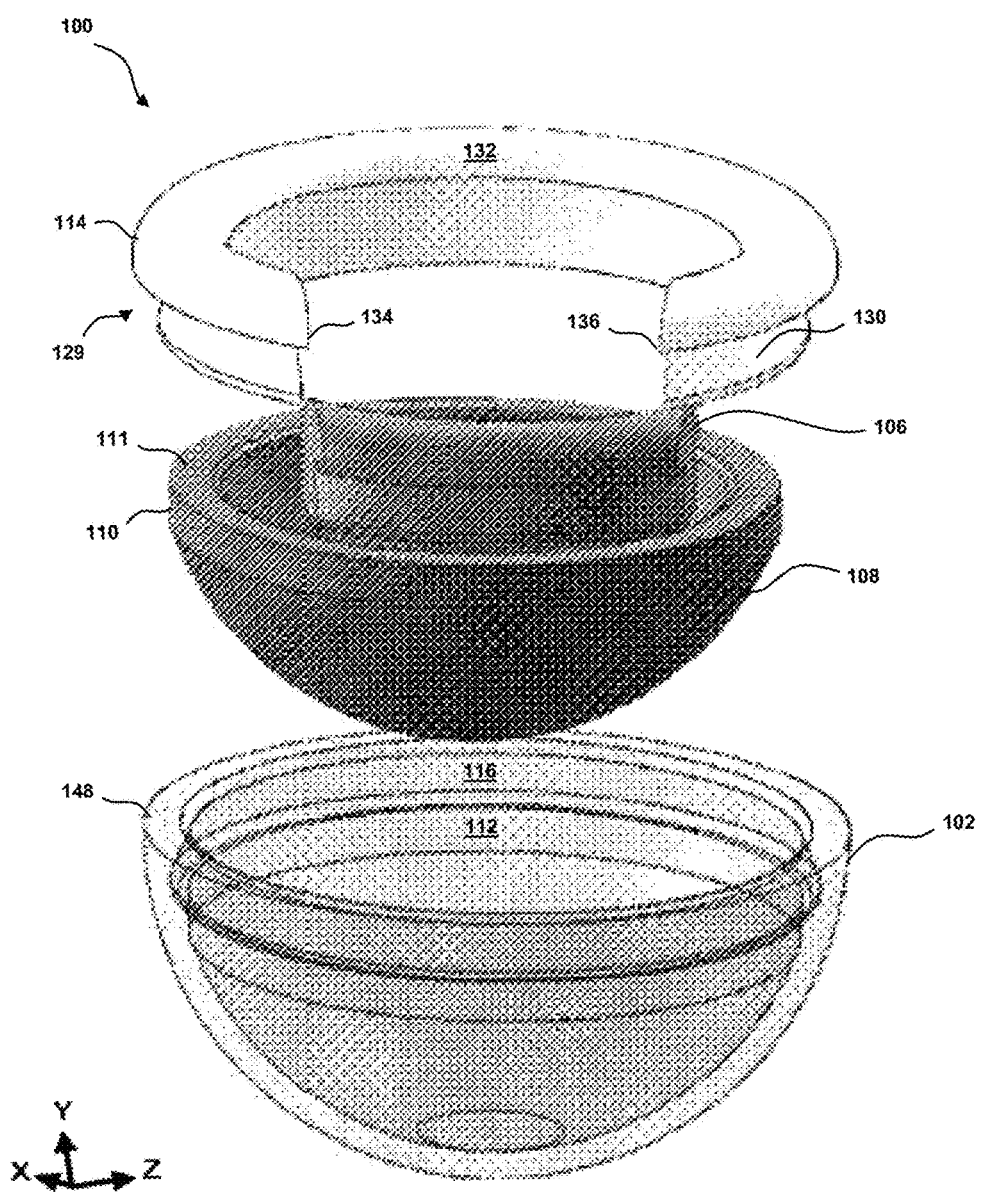
FIG. 9 is a pre-assembly perspective view of the component of FIGS. 1 and 8.

FIG. 8 schematically illustrates exemplary assembly of component 100. Polar portion 108 of hybrid bearing 104 is inserted into acetabular cup 102. Rim bearing 114 is next inserted into cup 102, atop rim 111 of polar portion 108. For example, free ends 134 and 136 are pressed towards one another to reduce effective circumference of rim bearing 114 and to facilitate alignment of groove 129 and angled sidewall 130 with reverse tapered portion 116. Once rim bearing 114 is inserted into cup 102 against portion 116 and with lip 132 covering cup rim 148, locking component 106 is inserted between free ends 134 and 136. FIG. 9 further illustrates alignment of locking component 106 with a gap between free ends 134 and 136.

Figure 10:
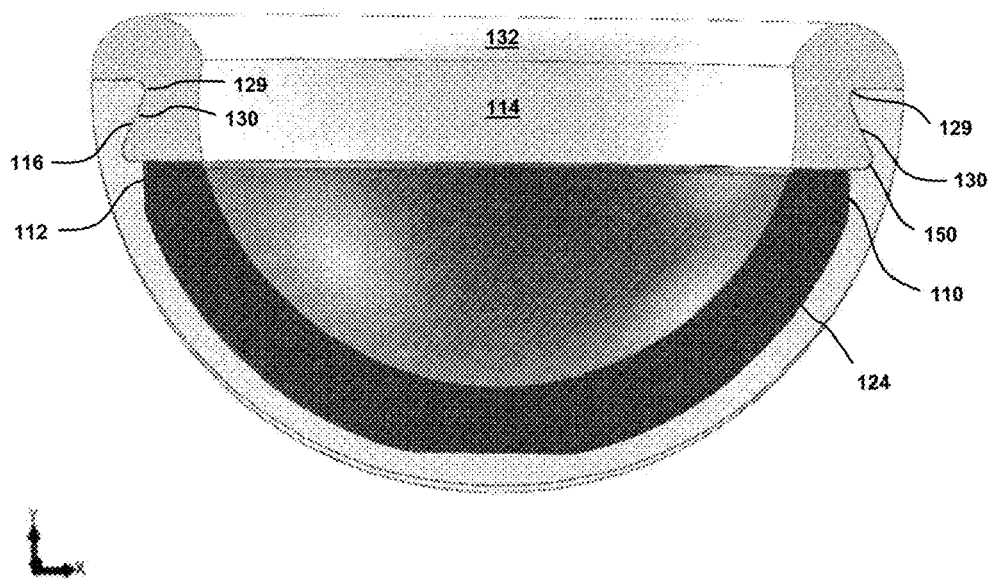
FIG. 10 is a cross-sectional view of a hybrid bearing surface acetabular component, taken along line A--A of FIG. 1.

FIG. 10 is a cross-sectional view of an assembled hybrid bearing surface acetabular component, taken along line A--A, FIG. 1 and illustrating fit of edge 110 of polar portion 108 against morse taper type profile 112 of cup 102 and fit of rim bearing 114 with and above reverse taper portion 116 of cup 102. As shown, rim 111 of polar portion 108 and a mid-lip 150 of cup 102 may provide combined support for rim bearing 114 when inserted in cup 102 atop polar portion 108.

Figure 11:
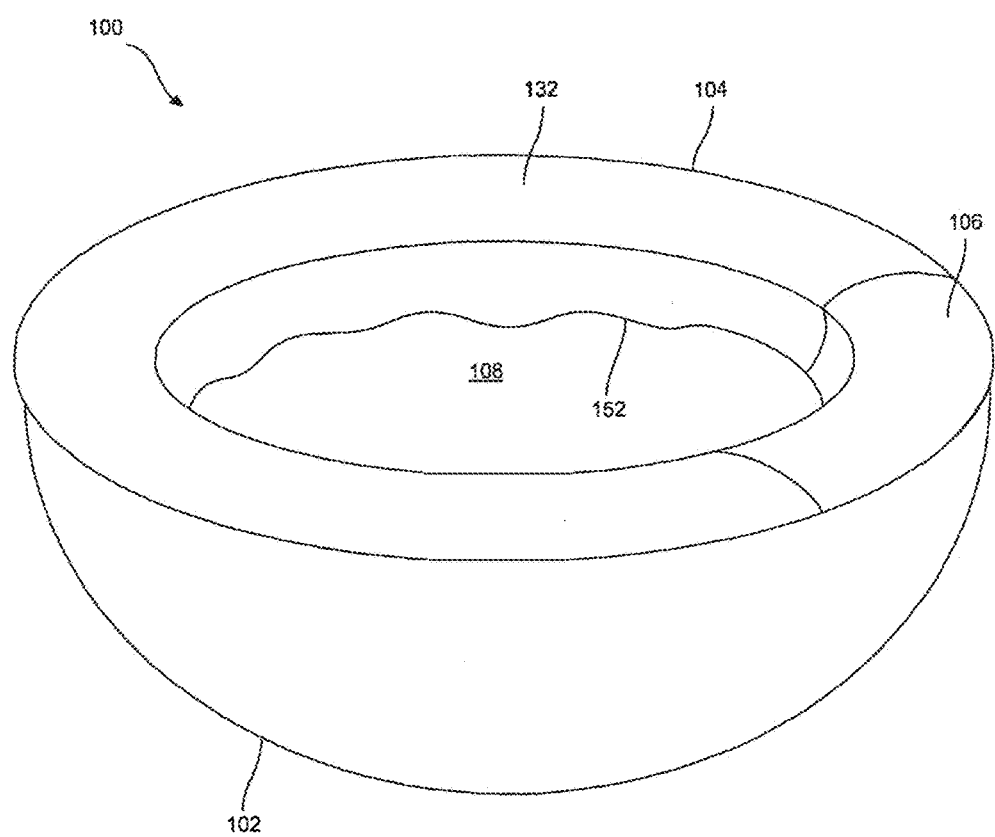
FIG. 11 is a perspective view of the component of FIG. 1, including an irregular boundary between a polar portion and a rim portion of the hybrid bearing, according to an embodiment.

As schematically shown in FIG. 11, polar portion 108 and rim bearing 114 may have complementary, undulating or interweaving surfaces to form an irregular boundary 152 there between when polar portion 108 and rim bearing 114 are in place within cup 102. Rim 111 of polar portion 108 and a base 154 of rim bearing 114 (see FIG. 5) may include complementary undulations, surface features and/or lock and key features to further secure hybrid bearing 104 together. A base of keystone element 106 (base not shown) may include features similar to base 154 to provide continuous base geometry, or the keystone element 106 base may include unique surface features for alignment with a particular and complimentary area of rim 111 of polar portion 108. Irregular boundary 152 may provide a smooth, less abrupt transition of the femoral head between bearing materials, thus reducing stress concentration. Locating the boundary between rim bearing 114 and polar portion 108 within acetabular cup 102 further manages stress concentration. Alternately or additionally (and regardless of boundary 152 regularity or irregularity), rim bearing 114 may be designed with a smaller radius of curvature/internal diameter than polar bearing 108, allowing rim bearing 114 to stand proud of polar bearing 108 at the interface between the two. Thus, the relatively tougher, more compliant material of rim bearing 114 (as opposed to polar portion 108) accepts the burden of any stress increase that might be caused by the boundary between bearing materials. Rim bearing 114 may also have a tighter radius of curvature in the "z" direction than polar bearing 108, thereby curving into the femoral head and holding it against articular surface 128 to prevent the femoral head from rolling up and outward.

Figure 12:
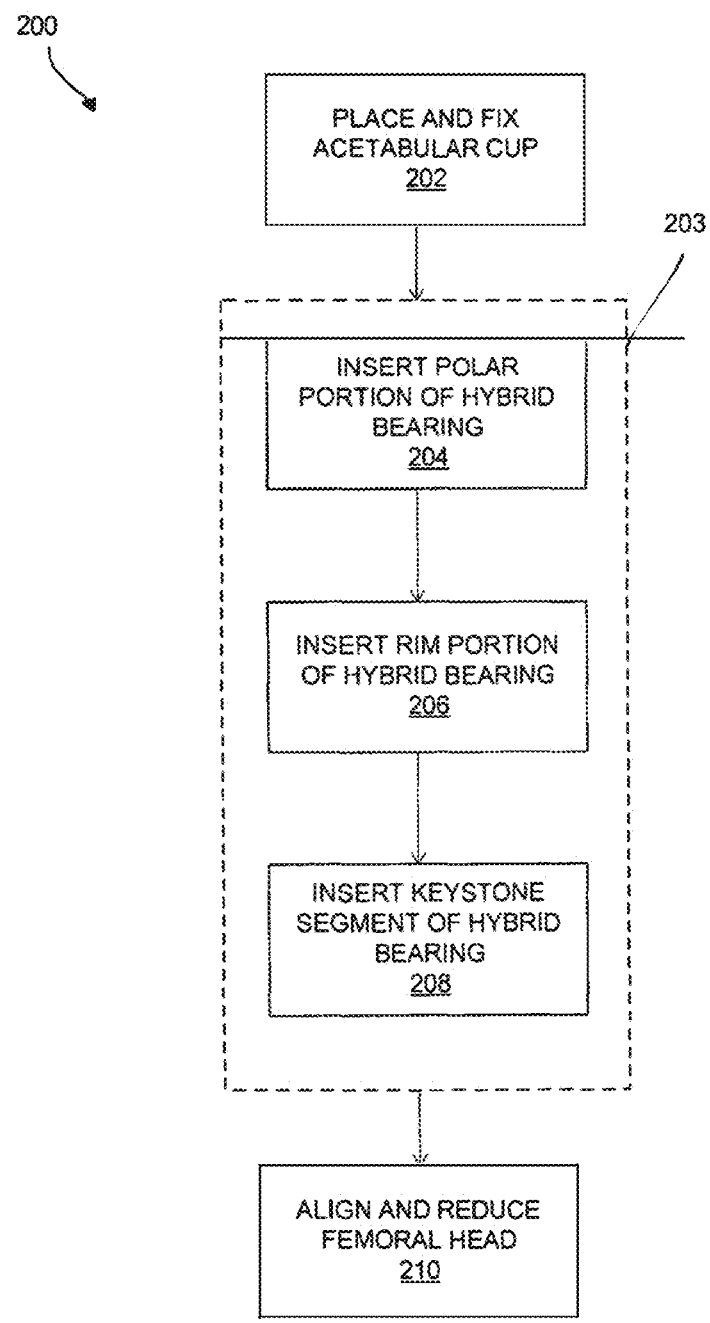
FIG. 12 is a flowchart illustrating a method of installing an artificial hip, according to an embodiment.

FIG. 12 shows an exemplary method 200 of installing an artificial hip. In step 202, an acetabular cup is placed and secured with a patients acetabulum, for example using bone cement or other medium or method known in orthopedic surgery. A hybrid bearing is placed with the acetabular cup in steps 204-208 (outlined by dotted box 203). In step 204, a polar portion of the hybrid bearing is inserted into the acetabular cup such that outer surfaces of the polar portion contact or approximate an inner base and surfaces of the acetabular cup. The exterior of the polar portion may be complementary to the interior of the acetabular cup, for example having a bowl or cup shape.

In step 206, a rim bearing is inserted into the acetabular cup such that a base of the rim bearing rests upon a rim of the polar portion and a lip of the rim bearing overlaps a rim of the acetabular cup. Insertion of the rim bearing may include compressing open ends of the rim bearing together to reduce effective circumference of the rim bearing, and advancing the rim bearing into the acetabular cup. Where the rim of the polar portion and the base of the rim bearing include complementary lock and key or other alignment features, the rim bearing is placed with the polar portion in a specific orientation.

A keystone segment is inserted between open ends of the rim bearing, and such that a lip of the keystone segment overlaps the rim of the acetabular cup left exposed between the open ends of the rim bearing, in step 208. The keystone element may be pushed or snapped into place between the open ends. Optionally, protrusions (i.e., lugs) on an outer surface of the keystone element are aligned with select holes or indentations of a series of holes or indentations lining at least a portion of the acetabular cup, to customize position of the rim bearing and keystone element and to prevent rotation of the rim bearing (and optionally, the entire hybrid bearing) within the cup, once the keystone element is in place. Still optionally or alternatively, an adhesive may be used to secure keystone element in place with respect to the acetabular cup.

Following placement of the hybrid bearing, and optionally, any drying time, the head of the femur is aligned with the socket formed by the hybrid bearing, and the femur is reduced into the socket, in step 210.

It will be appreciated that steps of inserting the hybrid bearing (box 203) may vary in order. For example, the keystone segment may be placed with the acetabular cup and above the polar bearing (and optionally affixed with the acetabular cup) before placement of the rim bearing. It will also be appreciated that method 200 does not specify pre-placement steps of surgery, placement of a femoral head with the femur or other routine surgical steps (e.g., suction, cleaning and closure).

Intra-operative placement of hybrid bearing 104 with acetabular cup 100 allows a surgeon to customize placement of keystone element 106 and/or rim bearing 114 with respect to acetabular cup 102. For example, rim bearing 114 may be axially asymmetrical to allow a surgeon to establish a best fit with other hip device components or with individual anatomy. In another embodiment, acetabular cup 102 may be pre-assembled with polar portion 108 and rim bearing 114, such that the entire hybrid bearing surface acetabular component 100 may be placed and affixed as a single unit.

Figure 13:
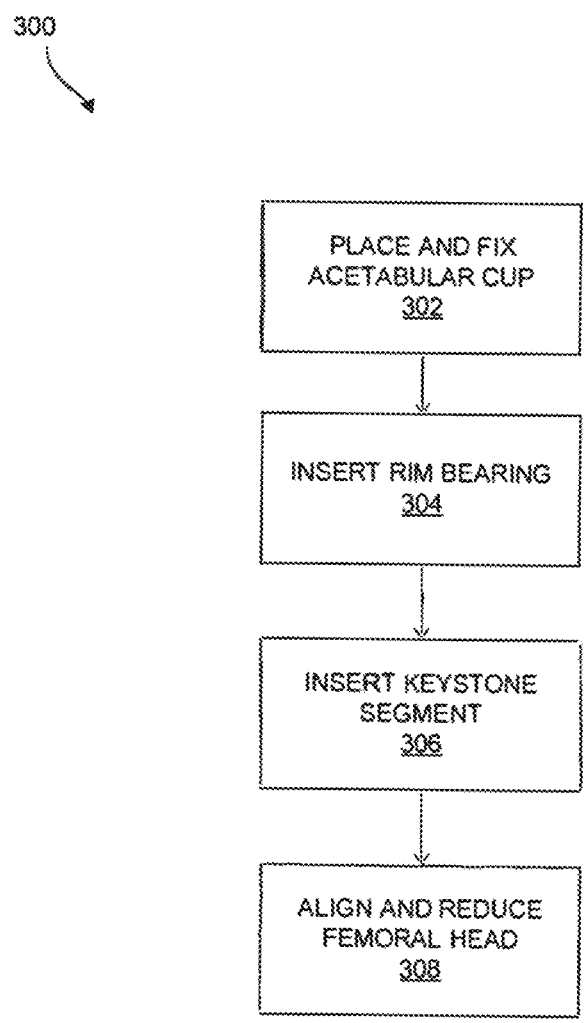
FIG. 13 is a flowchart depicting a method of installing an artificial hip utilizing a rim bearing, according to an embodiment.

FIG. 13 shows an exemplary method 300 of installing an artificial hip where the polar bearing is integral to the acetabular cup. For example, in one aspect of the invention, polar bearing 108 may be omitted and its geometry machined into or otherwise formed with the acetabular cup. The acetabular cup itself thus provides a circumferential inner shelf or ledge to support a circumferential base of the rim bearing (i.e., rim bearing 114). The inner ledge may include surface features or geometry for mating with base features of the rim bearing, to further enhance fit and security of the rim bearing within the acetabular cup.

In step 302, an acetabular cup is placed and secured with a patient's acetabulum, for example using bone cement or other known medium or method. A rim bearing is inserted into the acetabular cup in step 304, and a keystone inserted in step 306. In one example of steps 304 and 306, open ends of rim bearing 114 are pressed together to reduce effective circumference of the rim bearing, and the rim bearing is placed with an upper section of the acetabular cup (similar to section 122 of cup 102). Rim bearing 114 for example rests upon an internal circumferential shelf or edge machined into the acetabular cup. Exterior groove 129 and sidewall 130 of the rim bearing may be fitted against a reverse tapered portion of the upper section (similar to reverse tapered portion 116 of cup 102). When in place, lip 132 of rim bearing 114 covers a rim of the cup (similar to rim 148) to prevent contact between the hard cup rim and a femoral head. Keystone segment 106 is placed in the upper cup section between open ends of the rim bearing. In one aspect, external surface features (e.g., protrusions) are selectively mated with complementary mating features (e.g., indentations or holes) inside the cup, for customizing position of the rim bearing and keystone element with the cup. When in place, lip 144 of keystone segment 106 covers the cup rim.

The femoral head is aligned with the acetabular cup and rim bearing and reduced into place, in step 308.

Figure 14:
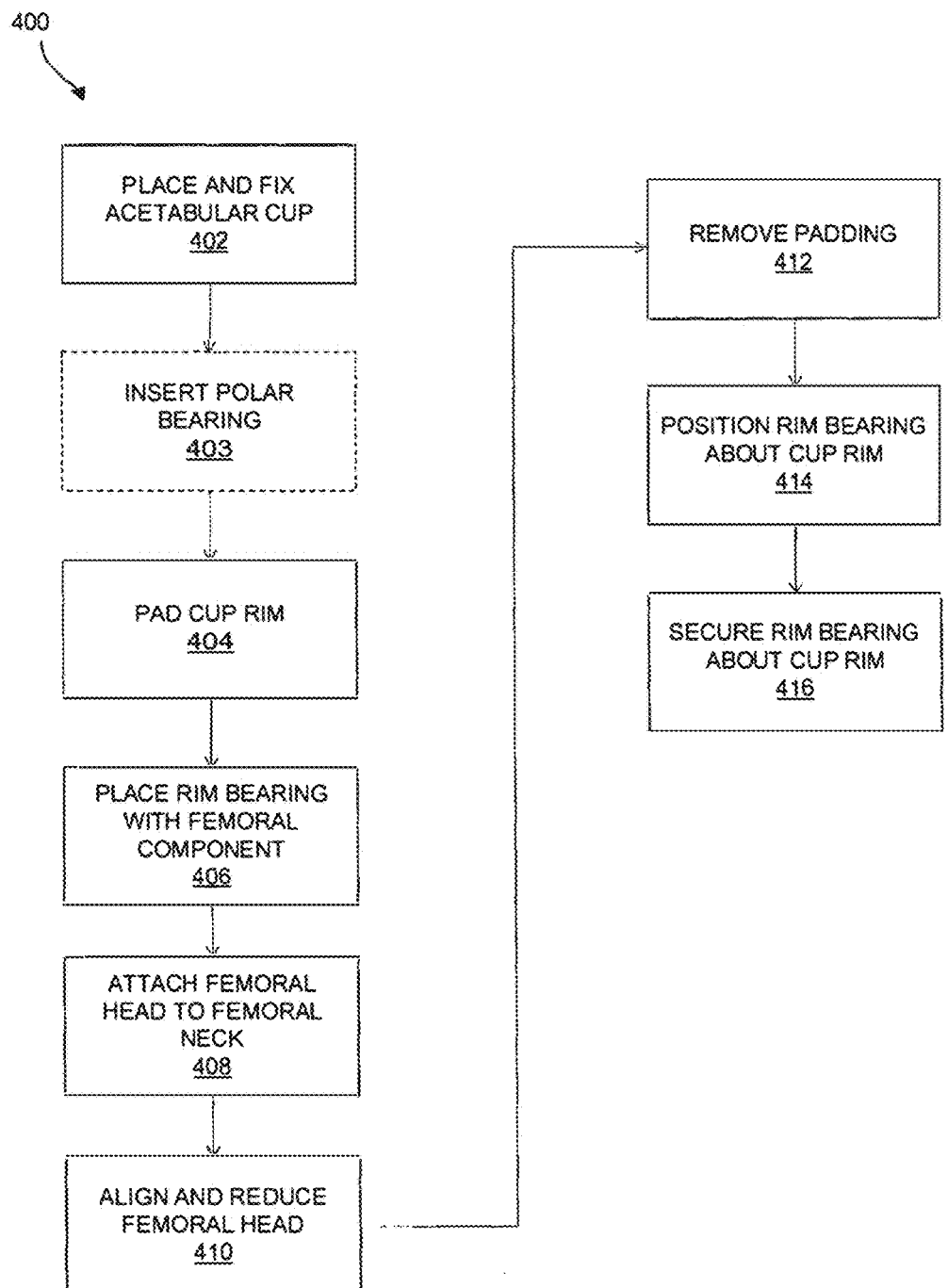
FIG. 14 is a flowchart showing a method of installing an artificial hip, according to an embodiment.

FIG. 14 shows an alternative method 400 of installing an artificial hip. An acetabular cup is placed and secured with a patient's acetabulum in step 402. A polar bearing, such as polar portion 108, is inserted into the cup in optional step 403. It will be appreciated that step 403 may be unnecessary where the polar portion is machined into or otherwise integral to the acetabular cup. In step 404, the cup rim is padded to prevent contact of a femoral head on the hard cup rim. In one example of step 404, a temporary protective apron of a strong and resilient material is placed about the cup rim. The apron is for example a thin sheet of material that has high toughness and a low coefficient of friction, and is flexible in sheet form. Thus, the apron provides a non-damaging, low friction path for the femoral head to move from its dislocated position, over the hard cup rim and into its fully reduced position in the bearing. Exemplary apron materials include ultrahigh molecular weight polyethylene, high density polyethylene, low density polyethylene, Delrin, Nylon, polypropylene and other polymers. The apron may be shaped as an annular ring. Alternately, the apron may form a "c" shape with the opening of the "c" ranging from a small slit to a larger opening. Where the apron is a "c" shape, step 404 includes placing the opening away from the direction of approach of the femoral head during reduction.

A rim bearing is placed with a femoral component, in step 406, and the femoral head is attached to the femoral neck, in step 408. In one example of steps 406 and 408, rim bearing 114 is placed about the femoral neck prior to nailing or otherwise attaching the femoral neck to the femoral head.

The femoral head is aligned with the acetabular cup and reduced into place, in step 410. The apron or other padding about the cup rim prevents contact between the femoral head and the rim during reduction. Once reduction is satisfactorily completed, the padding is removed, in step 412. In one example of step 412, an annular ring apron is cut through and removed. In another example of step 412, a "c" shaped apron is pulled from the cup.

The rim bearing is positioned about the cup rim, in step 414. In one example of step 414, rim bearing 114 is drawn onto the rim of the cup and secured in place, in step 416. In one example of step 416, the rim bearing is secured in place using a keystone element, as described herein. In another example of step 416, rim bearing 114 is a continuous ring, and a keystone element such as element 106 is not used to secure the bearing in place. Rather, complementary lock-and-key features between the rim bearing and acetabular cup may be mated together to secure the rim bearing in place, a fixative may be used and/or geometry and elastic properties of the rim bearing may bias the rim bearing against the acetabular cup.

While the present invention has been described above, it should be clear that many changes and modifications may be made to the component and related methods without departing from the spirit and scope of this invention. Likewise, features described with respect to a disclosed method may also apply to components and systems herein, and vice versa.

What is claimed is:

1. An acetabular component comprising a hybrid bearing, the hybrid bearing configured to fit into an acetabular cup having a first inner circumference comprising a reverse tapered portion, said hybrid bearing comprising:
   a) a polar bearing;
   b) a rim bearing, wherein the rim bearing is arc-shaped to allow reduction in effective circumference of said rim bearing and to facilitate insertion of said rim bearing into said acetabular cup; and
   c) a locking component for securing said rim bearing radially against said acetabular cup, wherein said locking component fits between two ends of the arc-shaped rim bearing to secure the rim bearing against said reverse tapered portion of said acetabular cup;
   wherein an interior surface of said polar bearing and an interior surface of said rim bearing form a hybrid bearing surface configured to contact a proximal femoral head.

2. The acetabular component of claim 1, wherein said rim bearing comprises an exterior circumferential groove and an angled sidewall for fitting with said reverse tapered portion of said acetabular cup.

3. The acetabular component of claim 1, wherein said rim bearing further comprises a lip for covering a rim of said acetabular cup.

4. The acetabular component of claim 3, wherein said locking component comprises a lip for covering said rim of said acetabular cup between the two ends of the rim bearing.

5. The acetabular component of claim 1, wherein said interior surface of said polar bearing and said interior surface of said rim bearing form a circumferential boundary.

6. The acetabular component of claim 5, wherein said circumferential boundary is straight.

7. The acetabular component of claim 5, wherein said circumferential boundary is undulating.

8. The acetabular component of claim 1, wherein the polar bearing comprises a rim and a lower body, and wherein the interior surface of the polar bearing comprises a chamfered inner edge between the rim and an interior of the lower body.

9. The acetabular component of claim 1, wherein said polar bearing comprises a hard material and said rim bearing comprises a compliant material, wherein said hard material is harder than said compliant material.

10. The acetabular component of claim 1, wherein said interior surface of said polar bearing comprises metal or ceramic.

11. The acetabular component of claim 1, wherein said interior surface of said rim bearing comprises ultra-high molecular weight polyethylene.

12. A system comprising an acetabular component and an acetabular cup having a first inner circumference comprising a reverse tapered portion, the acetabular component comprising a hybrid bearing, the hybrid bearing configured to fit into the acetabular, said hybrid bearing comprising:
   a) a polar bearing;
   b) a rim bearing, wherein the rim bearing is arc-shaped to allow reduction in effective circumference of said rim bearing and to facilitate insertion of said rim bearing into said acetabular cup; and
   c) a locking component for securing said rim bearing radially against said acetabular cup, wherein said locking component fits between two ends of the arc-shaped rim bearing to secure the rim bearing against said reverse tapered portion of said acetabular cup;
   wherein an interior surface of said polar bearing and an interior surface of said rim bearing form a hybrid bearing surface configured to contact a proximal femoral head.

13. The system of claim 12, wherein said acetabular cup comprises a taper present about a second inner circumference of said acetabular cup.

14. The system of claim 12, wherein said acetabular cup comprises a biocompatible metal.

* * * * *

UNITED STATES PATENT AND TRADEMARK OFFICE
CERTIFICATE OF CORRECTION

| | |
|---|---|
| PATENT NO. | : 10,085,840 B2 |
| APPLICATION NO. | : 14/377698 |
| DATED | : October 2, 2018 |
| INVENTOR(S) | : Currier et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 702 days.

Signed and Sealed this
Tenth Day of December, 2019

Andrei Iancu
*Director of the United States Patent and Trademark Office*